United States Patent [19]

Dempsey et al.

[11] Patent Number: 5,417,222
[45] Date of Patent: May 23, 1995

[54] PATIENT MONITORING SYSTEM

[75] Inventors: Michael K. Dempsey, Acton; Mark S. Kotfila, Chelmsford, both of Mass.

[73] Assignee: Hewlett-Packard Company, Palo Alto, Calif.

[21] Appl. No.: 185,532

[22] Filed: Jan. 21, 1994

[51] Int. Cl.$^6$ .................................... A61B 5/0402
[52] U.S. Cl. ................................. 128/696; 128/903
[58] Field of Search ............. 128/696, 709, 710, 903, 128/904

[56] References Cited

U.S. PATENT DOCUMENTS

| | | | |
|---|---|---|---|
| 4,356,486 | 10/1982 | Mount | 128/903 |
| 5,085,224 | 2/1992 | Galen et al. | 128/903 |
| 5,168,874 | 12/1992 | Segalowitz | 128/903 |

*Primary Examiner*—George Manuel

[57] ABSTRACT

A method and apparatus for performing patient monitoring which interfaces a telemetry monitor with a standard portable computer (such as a laptop computer, palmtop computer or personal digital assistant) with the display and the keyboard or other device of the portable computer being utilized to provide both display and input capability to the telemetry monitor. The telemetry monitor is provided with an I/O port which is interfaceable with an I/O port of the portable computer to permit operation as indicated above. Inputs from the user may also be passed through the interface ports and the transmitter of the telemetry monitor to a central station. A back channel may optionally be provided to permit information from the central station to be applied either to control the telemetry monitor or to be passed through the interface ports to the portable processor to provide information to a user.

20 Claims, 1 Drawing Sheet

PATIENT MONITORING SYSTEM

FIELD OF THE INVENTION

This invention relates to patient monitoring systems and more particularly to a method and apparatus for utilizing a patient telemetry monitor interfaced to a standard portable processor to facilitate the collection and use of various patient related information, particularly in a hospital or other institutional setting.

BACKGROUND OF THE INVENTION

In the current economy, a key objective in hospitals and other institutions providing patient care is to maintain acceptable levels of such care while minimizing the costs. Since intensive care units (ICU's) and the bedside monitors maintained in such units are very expensive, efforts have been made to move patients out of ICU's to step-down units as soon as it is safe for the patient to do so and to utilize far less expensive telemetry monitors to monitor various physiological conditions of the patient rather than expensive bedside monitors.

However, there is a price to be paid for such reduced costs in various applications of such devices. In particular, telemetry monitors are designed to be worn by a patient and to permit the patient to have freedom of movement within at least selected areas of the institution while still being monitored. It is, therefore, desirable that these monitors be made as small and light in weight as possible. Since such monitors are battery-operated, an effort is also made to minimize drains on the battery(s). For these reasons, and also to reduce the costs of the units, telemetry monitors typically contain an appropriate physiological monitor/measuring device, a simple processor device (generally a microprocessor chip) which is hard-wired or programmed to suitably process information received from the monitor and convert it into suitable form for transmission and a radio frequency (RF) or other suitable transmitter for outputting the processed monitor information to a suitable receiver which leads to a central monitoring station, generally also located in the step-down unit. Such patient telemetry monitors do not, however, typically contain any type of display for displaying representations of the monitored outputs, nor do they contain any type of input device. At most, such devices may contain a single "panic" button which a patient may press in the event the patient is experiencing a problem and requires assistance and/or some type of simple display which provides an indication of electrode or battery condition for the monitors.

This lack of input capability and of display can create problems in a number of situations where such telemetry monitors are utilized and make such monitors far less versatile and their use far less desirable than would be the case if such facilities were available. Such situations include:

(a) When the monitors is being placed on the patient, a need exists to assure that the device is being properly mounting the desired signal. For example, where the telemetry monitors contains an ECG monitor, the medical personnel mounting the monitor must assure both that electrodes are properly positioned for the particular patient to provide desired outputs and that the electrodes are making good electrical contact. This can easily be determined by viewing the ECG output obtained from the monitor. However, since with a standard telemetry monitor such information appears only at for example the central nursing station in the hospital step-down monitors, the person mounting the telemetry monitor must position the electrodes and then run to the nursing station or call the nursing station to verify that they have been properly placed. This procedure may require several iterations before the electrodes are properly placed, making the mounting operation take far more time, be far more complicated, involve more people and be much more expensive than it need be.

(b) A second situation where lack of display is a problem is where a patient is experiencing a problem. With current apparatus, when personnel arrive at the scene where a patient is experiencing problems, they must bring a cumbersome and expensive monitoring device with them and hook the monitoring device up to the patient before they can obtain a visual indication of the exact nature of the patient's problem and determine if remedial steps they are taking are alleviating the problem. This can cause precious time to be lost while the equipment is located and transported to the location where the patient is experiencing difficulty and additional time to be lost while the new equipment is being hooked up to the patient. It would be preferable if such information were immediately available from the existing telemetry monitor already hooked up to the patient.

(c) Still another situation where the lack of display for these devices is a problem is where a doctor or nurse is making rounds or, in a teaching hospital, where a doctor is taking students on rounds. With the current situation, physiological information such as a patient's temperature and pulse can be taken in the patient's room, but the doctor or nurse must go to a central nursing station to view the physiological information from the monitor, for example ECG information.

(d) Similar problems arise during drug induction (i.e., for vasoactive drugs there is a requirement to watch the patient's ECG for adverse affects) or routine monitoring and during troubleshooting of the hardware or of a physiological problem of the patient where the person doing such troubleshooting is basically operating blind.

The lack of an input capability is also a problem in that it is not possible to easily change the mode of operation of the monitor, to cause the processor in the telemetry monitor to process information differently before transmission, or to input additional information at the patient's bedside to be transmitted with the monitor output to the central station, either for viewing by personnel at that station or for storage with the patient's records. For example, when a nurse is doing rounds, it would be desirable if the nurse could input physiological readings such as temperature, pulse and the like taken by the nurse and have this information transmitted for storage with the patient's records along with the ECG or other physiological information on the patient being transmitted by the telemetry monitor. Such an input capability would speed the flow of data into the system, since otherwise such information would get into the system only from a downloading of a suitable machine carried by a doctor or nurse at the end of the rounds or from transcription and manual data entry of handwritten notes taken by such medical personnel during rounds, and would therefore improve patient care and reduce the likelihood of errors occurring. For example, particularly if a back channel capability from the central station were also provided, if a reading differed significantly from prior readings, an indication could be provided to the doctor or nurse doing the examination to recheck such reading to assure that it is not an error. A back channel capability would also permit additional information concerning the patient to be provided to the medical personnel doing rounds, or to medical personnel responding to an emergency so as to assure that necessary diagnostic procedures are performed and that the patient receives proper treatment. For example, in an emergency situation, the responding personnel could be alerted to drug allergies which a patient may have or to special care which the patient may require in such emergency situations. During rounds, a knowledge of the patient's specific condition would assure that appropriate readings are taken on the patient so that the particular problems of the patient are properly monitored.

However, while the input-output and display capabilities discussed above are desirable for a telemetry monitor, it is still desirable that such capabilities be achievable without any significant increase in the monitor's cost, size, weight and battery usage. As of this time, a solution which meets these contradictory objectives does not exist.

SUMMARY OF THE INVENTION

In accordance with the teachings of this invention, the objective of providing a display and input-output capability for a telemetry monitor without significantly increasing its cost, size, weight and battery usage is met by providing an interface for such monitors with a standard portable computer such as a laptop computer, palmtop computer (for example the Hewlett Packard 100LX), or personal digital assistant (PDA) with the display and the input keyboard (and/or other input device) of the portable computer being utilized to provide both display and input capability to the telemetry monitor. More specifically, the telemetry monitor, which includes a physiological monitor, such as an ECG monitor, for monitoring at least one selected physiological condition of the patient, also includes a transmitter for transmitting information related to the monitor output and an input-output (I/O) port to which information relating to the monitor output is also applied. The portable processor has an input device such as a keyboard, a display, and an input-output port which is interfaceable with the I/O port of the telemetry monitor. When the I/O ports of the telemetry monitor and the processor are interfaced, for example through an RF link, infrared (IR) or other optical link, or by means of a wire connected to the two ports, the processor receives monitor related information from the telemetry monitor and causes a selected indication of such information to be displayed on its display. Since some medical personnel already carry a portable processor such as a palmtop computer or PDA at all times, this interfacing capability greatly expands the usefulness of the telemetry monitor without significantly increasing its size, weight, cost or battery usage, and without requiring a substantial change in the way medical personnel operate.

At least selected information inputted at the input device of the processor may also be applied through its I/O port to the telemetry monitor and the telemetry monitor may selectively utilize such inputted information. For example, the information may be passed to the telemetry monitor's transmitter for transmission to a central station or may be utilized to change its mode of operation or to otherwise control the operation of the monitor. A monitor may for example be utilized to monitor a plurality of different physiological conditions, with a received input being utilized to control the physiological condition being monitored.

The telemetry monitor may also contain a receiver for inputs from the central station. Data received at the telemetry monitor from the central station may be applied by the telemetry monitor to control the operation of its physiological monitor and selected such data may also be passed through the interfaced I/O ports to the portable processor to provide selected information to medical personnel utilizing the system or to otherwise be selectively utilized at the processor.

The foregoing and other objects, features and advantages of the invention will be apparent from the following more particular description of a preferred embodiment of the invention as illustrated in the accompanying drawings.

DETAILED DESCRIPTION

Figure 1:
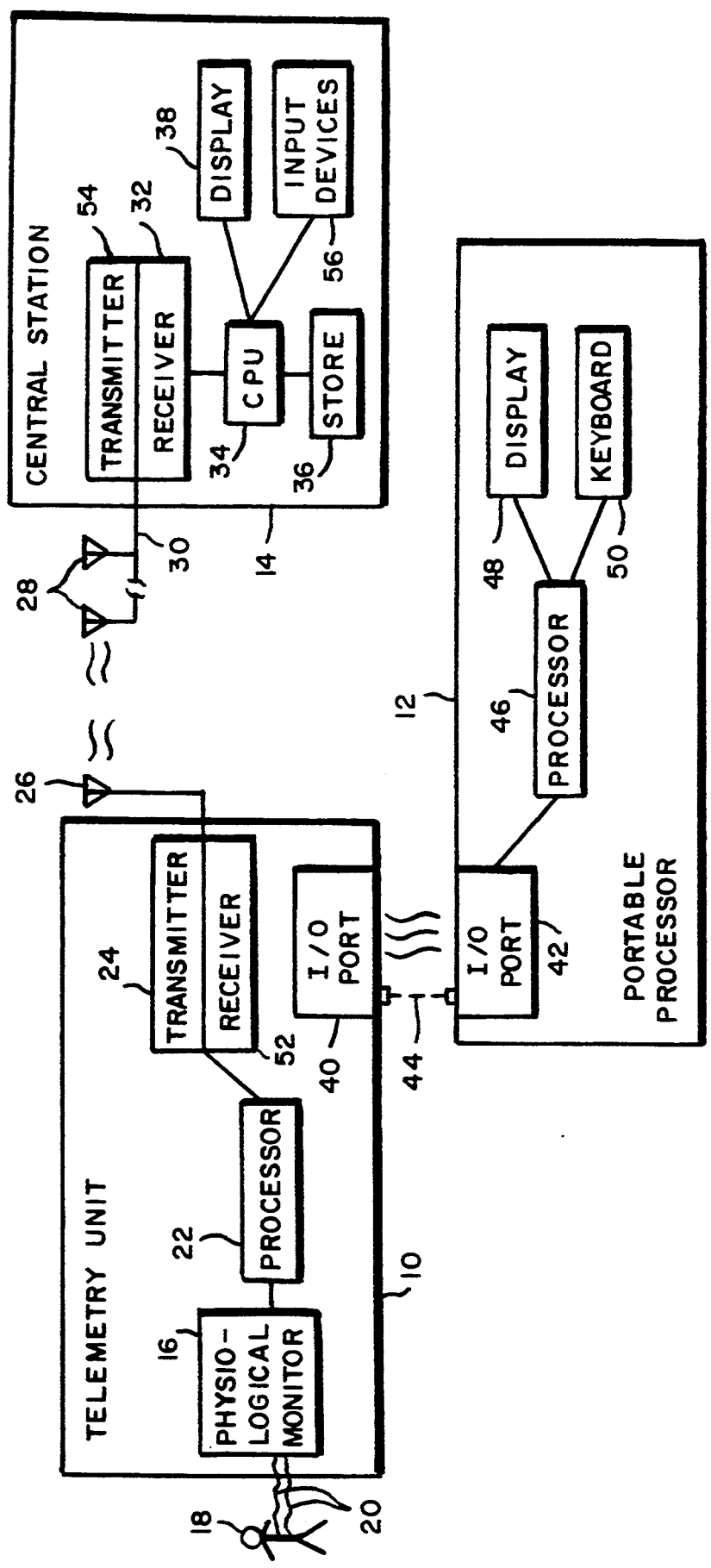
FIG. 1 is a block schematic diagram of the components utilized in accordance with a preferred embodiment of the invention.

As discussed above, the invention provides an I/O capability and a display output for a telemetry monitor without requiring any significant increase in the size, weight, cost or battery usage of such monitor by permitting the monitor to be interfaced with a conventional portable processor, and utilizing the portable processor's display to display outputs from the telemetry monitor and utilizing the portable processor's keyboard or other input devices as input elements to the telemetry monitor. Thus, referring to FIG. 1, a telemetry monitor 10 is shown interfaced to a portable processor 12. Telemetry monitor 10 may be any of a variety of devices of this type which are intended to monitor one or more selected physiological conditions of the patient and to transmit readings taken by the monitor to a nursing station or other central station 14. Monitor 10 typically contains a physiological monitor (or monitors) 16 which may for example be an ECG monitor for a heart patient, an SP02 monitor for an emphysema patient, a brainwave monitor for an epileptic patient, and/or other suitable physiological monitor depending on patient condition. The physiological monitor 16 would be suitably connected to the patient 18 by leads 20. For example, with an ECG monitor, the leads 20 would be connected to electrodes attached to the patient's chest.

Readings taken by monitor 16 are fed to a processor 22 which is preferably either a suitably programmed microprocessor or a special purpose processor which converts the outputs received from monitor 16 to a suitable form for transmission to central station 14. Depending on the telemetry monitor 10, processor 22 may also contain selected information concerning the patient, add error checking data to the output, process received data to a more useful form (i.e., get heart rate) etc.

The output from processor 22 is fed to a transmitter 24 which feeds the output to a suitable output antenna 26 or other suitable transmitting element. Depending on the telemetry system in the hospital or other institution, transmitter 24 and output device 26 may be IR elements, RF elements or other suitable radiation transmitting element. Radiation outputted by antenna or other output element 26 is received by the closest one or more of receiving antenna or other receiving devices 28 suitably positioned in at least the monitor where the patient is located.

Receiving elements 28 are connected through a line 30 to a receiver 32 at central station 14. Information received at receiver 32 is applied to a CPU 34 which may be at the central station or at another suitable location in the institution. CPU 34 may perform further processing on the received information and may selectively store such information, either as received or in processed form in temporary or bulk storage devices 36 and may cause images indicative of such received information to be selectively displayed on one or more displays 38 at the central station. Thus, nurses or other medical personnel at the central station may monitor relevant physiological conditions of the patient. Since telemetry monitors 10 are typically relatively small and battery-powered, the patient may move freely about areas containing receiving antennas or other elements 28 while still permitting the continuous monitoring of relevant patient physiological conditions.

What has been described to this point is a typical hospital telemetry system. However, as mentioned earlier, these systems have a number of deficiencies. Since to minimize size, weight, cost, and drain on the batteries, telemetry monitors 10 do not typically have displays, medical personnel connecting leads 20 a patient 18 are unable to obtain feedback readings to assure that such leads are properly placed and securely attached so as to provide the desired readings. The person mounting a monitor 10 must therefore initially attach the leads to appropriate locations and then walk to or call central station 14 to verify that the leads have been properly placed to obtain desired information for the particular patient 18. If the display on display 38 indicates that the leads have not been properly placed, the person must return to the patient, reposition the leads and then walk back to or call central station 14 to verify the new placement. Several iterations of this process may be required before all leads are properly attached. However, even with this tortuous process, leads may turn out to be only suitably attached rather than optimally attached since the instant feedback required for optimum positioning of leads is not possible.

Further, when it is determined at central station 14 that the patient 18 is experiencing a medical emergency, for example that the patient is going into cardiac arrest, readings taken by monitor 16 cannot be utilized by medical personnel sent to assist the patient. Therefore, such medical personnel must bring bedside monitoring equipment containing a display, or preferably a defibrillator containing an ECG monitor and display, with them so that they can determine on the spot the exact nature of the patient's problem and the patient's response to administered therapy. This results in the added expense of the hospital needing to maintain expensive monitoring equipment available for emergencies, slows the response to an emergency in that the responding medical personnel must first retrieve the defibrillator (which may not otherwise be required) or other monitoring equipment and must move this frequently large and heavy equipment to the patient's site and introduces a further delay in that the monitoring equipment must be attached to the patient or the electrodes on the patient before remedial procedures are initiated. This lost time, which would typically be several minutes, may be critical in determining whether the patient will survive.

The lack of readout capability from telemetry monitor 10 also complicates the charting of the patient by nurses on rounds and the diagnosis, monitoring and treatment of the patient by physicians and other medical personnel at the patient's bedside.

The flexibility of telemetry monitors 10 is also handicapped by the lack of input capability to these monitors. Thus, it might be desirable to have a monitor 16 operating in different modes (i.e. diagnostic versus monitoring quality for an ECG monitor) or monitors 16 may be provided which are capable of monitoring a variety of physiological conditions. With such monitors, an input capability to permit switching between the various conditions being monitored is desirable. Further, it is desirable, when a nurse or other medical personnel is charting a patient, to be able to transmit readings and observations on the patient to central station 14 for analysis and storage in store 36 as the readings are being taken rather than storing such information on the charting device or as handwritten notes and later either downloading or transcribing such information. Particularly if the storage capabilities of the portable processor being utilized by the medical personnel doing the charting is inadequate to store the quantity of data accumulated on rounds, or such processor is not used, so that the information must be otherwise recorded and then entered into the or such processors not used, system at central station 14 when rounds are completed, the subsequent transcription of previously recorded information can introduce a potential source of error into the process.

There are numerous other situations when either a display and/or input capability for telemetry monitor 10 would be desirable. For example, both capabilities are desirable when attempting to perform diagnostics on patient 18 or attempting to troubleshoot monitor 10. However, the added size, weight, cost and battery drain of such capabilities has heretofore prevented their being made available on telemetry monitors. This invention overcomes the above problem by adding only an I/O port 40 to telemetry monitor 10. Port 40 may for example be a port complying with Hewlett Packard's SIR protocol.

For one preferred embodiment, port 40 is an IR transmitter which interfaces with an IR receiver 42 which is already present on many palmtop, laptop and other portable processors currently available on the market. An example of a palmtop processor containing this capability and suitable for use as the portable processor 12 is a Hewlett Packard 100LX palmtop processor. Alternatively, a wire 44 may be connected between suitable terminals on I/O ports 40 and 42 to effect suitable interfacing between these ports. Another alternative is for ports 40 and 42 to be an RF transmitter and an RF receiver respectively. RF links are advantageous in some applications because of their greater range (up to approximately 75'), permitting for example, patient monitoring without disturbing the patient when the patient may be laying on the monitor and monitoring from outside the patient's room.

Port 42 is connected to provide information to processor element 46 of portable processor 12. Processor 46 contains some storage capability for storing information applied thereto and may also be programmed to perform selected processing on the received data. For example, it may convert the data to suitable form for display i.e. convert raw heartbeat data into the waveform data of a standard ECG display. Trends may also be computed for storage and/or display in graphic, waveform or other suitable form and other selected processing may be performed. Processor 46 controls the display on a display device 48, which device may for example be a liquid crystal display or some other type of flat screen display. Thus, a representation of the information outputted from monitor 16 may be displayed on display 48 and the nature of this representation may be varied by a user as required by controlling processor 46. For example, such representation may be a waveform, chart, graph or other suitable representation. Such control may, for example, be provided by inputs from a keyboard 50. While not specifically indicated in FIG. 1, portable processor 12 may also have other forms of input devices such as a joystick, roller ball, touch screen, pen based input or the like.

Keyboard 50, or any other available input device on portable processor 12, may also be utilized, if ports 40 and 42 are bilateral ports, as an input device to telemetry monitor 10. Thus, keyboard inputs, either as generated, or as modified by processor 46, may be applied through I/O port 42 to I/O port 40, and from I/O port 40 to processor 22. Such inputs may, for example, be utilized to change the mode of monitoring by monitor 16 from for example diagnostic to monitoring quality for an ECG or, where monitor 16 is adapted for monitoring a variety of physiological conditions, to change the condition being monitored. To the extent the output from monitor 16 is being processed by processor 22, inputs from keyboard 50 may also be utilized to alter or control such processing. Such inputs may also be utilized to run diagnostic routines on the telemetry monitor to troubleshoot the monitor or for other suitable purposes. It is also possible for a medical person to enter data at keyboard 50 and to have such data pass through processor 46, ports 42 and 40 and processor 22 to transmitter 24 for transmission to control station 14. A nurse doing rounds may thus transmit all of her readings and assessments directly to CPU 34 for storage, display or other purposes, eliminating the need for a substantial storage capability in portable processor 12 and eliminating the need to transcribe handwritten notes.

An option which is available with the system is for telemetry monitor 30 to have a receiver 52 in addition to transmitter 24 and for central station 14 to also have a transmitter 54. Information transmitted by transmitter 54 would be radiated by antennas, IR transmitters or other suitable devices 28 and would be received at antenna or other suitable receiving device 26 which feeds receiver 52. Each message sent by transmitter 54 could begin with an encoded address so that it is received and/or utilized only by the one or more telemetry monitors for which it is intended.

This optional feature permits CPU 34 at central station 14, either in response to user commands on an input device 56 or in response to the CPU programming to transmit commands or information to processor 22. Such information or commands may be utilized to control monitor 16 or may be passed through ports 40 and 42 to processor 46. For example, a nurse on rounds or medical personnel responding to an emergency situation on patient 18 can either automatically receive or receive in response to a request generated on keyboard 50 selected information concerning patient 18, including the patient's prior medical history, drug allergies, and any special treatment instructions for the patient. The ready availability of such information can significantly enhance the effectiveness of medical personnel in treating a patient.

A system is thus provided which can increase productivity of nurses and other medical personnel by permitting monitor attachments and physiological readings to be made at the patient rather than requiring such personnel to go back and forth between the patient and the central nursing station in order to obtain such readings. It can also improve outcomes by providing more timely intervention in emergencies and can reduce costs both by permitting personnel to work more efficiently and by eliminating the need for expensive bedside mounted monitors and displays. It can also assure more timely and more accurate entry of patient information into the records of the institution. Greater flexibility in the use of telemetry monitors 10 is also possible since changes may be made in the operation of this monitor either in response to inputs from keyboard 50 of portable processor 12 or, where a back channel feature is also included, through the back channel from CPU 34. These substantial advantages are, however, achieved without substantially increasing the size, weight, battery use and cost of the telemetry monitor. Further, since medical personnel are often already carrying portable processors for other purposes, and will increasingly do so in the future, the benefits of this invention are also achieved without significant expense for added equipment and without significant change in the way medical personnel are already operating.

While the above discussion has been with reference to a preferred embodiment of the invention, and to various modifications thereof, it is apparent that this discussion is being presented by way of example. Therefore, telemetry monitor 10 and each of the components thereof may undergo further modification, the interface between the telemetry monitor and portable processor 12 may be any suitable interface available and the nature of portable processor 12 and of the various components thereof may vary as new products come on the market. Central station 14 may have all of the shown components located thereat or some such components may be at a central nursing station while other components, such as the CPU, are situated elsewhere and connected to the nursing station through suitable hardware. Thus, while the invention has been particularly shown and described above with reference to a preferred embodiment, the foregoing and other changes in form and detail may be made therein by one skilled in the art without departing from the spirit and scope of the invention.

What is claimed is:

1. A patient monitoring device comprising:
   a telemetry monitor, said monitor including a physiological monitor for monitoring at least one selected physiological condition of the patient, a transmitter for transmitting information related to the physiological monitor output, and an input/output port, information related to the physiological monitor output also being applied to said port; and
   a portable processor having an input device, a display and an input/output port which is interfaceable with the I/O port of the telemetry monitor, said processor receiving physiological monitor related information through its I/O port when the telemetry monitor and processor I/O ports are interfaced and causing a selected indication of said information to be displayed on said display.

2. A device as claimed in claim 1 wherein at least selected information inputted at said input device appears at the processor I/O port, said telemetry monitor receiving the selected information through its I/O port when said ports are interfaced and selectively utilizing said information.

3. A device as claimed in claim 2 wherein said telemetry monitor passes the received selected information to said transmitter for transmission to a central station.

4. A device as claimed in claim 2 wherein said telemetry monitor utilizes the received selected information to control the operation thereof.

5. A device as claimed in claim 4 wherein said received selected information is utilized to change the mode of operation of the physiological monitor.

6. A device as claimed in claim 5 wherein said physiological monitor may monitor a plurality of different physiological conditions, and wherein said received selected information controls the one or more physiological condition monitored.

7. A device as claimed in claim 1 wherein said ports are optical ports which are optically interfaced.

8. A device as claimed in claim 1 wherein said ports are wire sockets, said interfacing being done through an electrical wire.

9. A device as claimed in claim 1 wherein said ports are RF ports.

10. A device as claimed in claim 1 wherein said telemetry monitor includes a receiver for inputs from a central station.

11. A device as claimed in claim 10 wherein at least selected inputs to said receiver are applied by said telemetry monitor to control the operation of said physiological monitor.

12. A device as claimed in claim 10 wherein at least selected inputs to said receiver are passed through said I/O ports to said processor, said processor selectively utilizing said inputs.

13. A device as claimed in claim 1 wherein said monitor is an ECG monitor for monitoring the patient's heart function.

14. A device as claimed in claim 1 wherein said selected indication which is displayed is a waveform indication.

15. A method for obtaining and utilizing selected patient information comprising the steps of:
   attaching the physiological monitor of a telemetry monitor to the patient to obtain information on a selected physiological condition, said information being applied both to a transmitter and to an input/output port;
   interfacing the telemetry monitor I/O port to a compatible I/O port of a portable processor having an input device and a display;
   receiving said information at the processor through said I/O ports; and
   utilizing the processor's display to display at least a selected indication of said information.

16. A method as claimed in claim 15 including the steps of inputting information at the processors input device, passing at least selected portions of said inputted information through the I/O ports to the telemetry monitor, and selectively utilizing the inputted information at the telemetry monitor.

17. A method as claimed in claim 16 wherein said selectively utilizing step includes the step of transmitting selected portions of the inputted information to a central station.

18. A method as claimed in claim 16 wherein said selectively utilizing step includes utilizing the selected portion of the inputted information to control the physiological monitor.

19. A method as claimed in claim 15 including the steps of transmitting selected data from a central station, receiving the selected data at a receiver in said telemetry monitor, and utilizing the received data for at least one of (a) control the operation of the physiological monitor and (b) transmission through the I/O ports for selective utilization by the processor.

20. A method as claimed in claim 15 wherein the display obtained during said utilizing step is utilized during said attaching step to facilitate proper attachment of said physiological monitor to the patient.

* * * * *